(12) United States Patent
Ito et al.

(10) Patent No.: US 12,158,444 B2
(45) Date of Patent: Dec. 3, 2024

(54) GAS SENSOR ELEMENT AND GAS SENSOR

(71) Applicant: NGK Spark Plug Co., LTD., Nagoya (JP)

(72) Inventors: Kazuma Ito, Nagoya (JP); Takanori Ishikawa, Nagoya (JP); Hiroshi Isomura, Nagoya (JP)

(73) Assignee: NITERRA CO., LTD., Nagoya (JP)

( * ) Notice: Subject to any disclaimer, the term of this patent is extended or adjusted under 35 U.S.C. 154(b) by 748 days.

(21) Appl. No.: 17/418,605

(22) PCT Filed: Jul. 12, 2019

(86) PCT No.: PCT/JP2019/027679
§ 371 (c)(1),
(2) Date: Jun. 25, 2021

(87) PCT Pub. No.: WO2020/136962
PCT Pub. Date: Jul. 2, 2020

(65) Prior Publication Data
US 2022/0074887 A1    Mar. 10, 2022

(30) Foreign Application Priority Data
Dec. 28, 2018  (JP) ................. 2018-246600

(51) Int. Cl.
*G01N 27/407*   (2006.01)
*G01N 27/409*   (2006.01)
*G01N 33/00*    (2006.01)

(52) U.S. Cl.
CPC ..... *G01N 27/4077* (2013.01); *G01N 27/4075* (2013.01); *G01N 27/409* (2013.01); *G01N 33/0037* (2013.01)

(58) Field of Classification Search
CPC .......... G01N 27/4077; G01N 27/4075; G01N 27/409
See application file for complete search history.

(56) References Cited

U.S. PATENT DOCUMENTS 5,006,221 A * 4/1991 Uchikawa .......... G01N 27/4071
                                                    204/429
2010/0270155 A1  10/2010 Suzuki et al.
(Continued)

FOREIGN PATENT DOCUMENTS

JP    62-001163 U    1/1987
JP    01-119755 A    5/1989
(Continued)

OTHER PUBLICATIONS

International Search Report mailed Oct. 1, 2019 for the corresponding PCT International Patent Application No. PCT/JP2019/027679.

*Primary Examiner* — Alexander S Noguerola
(74) *Attorney, Agent, or Firm* — Leason Ellis LLP; Edward J. Ellis; Melvin C. Garner

(57) ABSTRACT

A gas sensor element includes a solid electrolyte body, a first electrode, a second electrode, and a protective layer. The protective layer includes at least a first catalyst layer that supports a first catalyst metal other than a metal facilitating a reduction reaction of nitrogen oxide and a second catalyst layer that supports only a second catalyst metal facilitating the reduction reaction of the nitrogen oxide. The first catalyst layer and the second catalyst layer are arranged in a path through which a gas under measurement is supplied from the outside of the gas sensor element to the first electrode in such a manner that the first catalyst layer and the second catalyst layer are not in direct contact with each other.

7 Claims, 5 Drawing Sheets

(56) References Cited

U.S. PATENT DOCUMENTS

2015/0060274 A1 3/2015 Ishikawa et al.
2017/0284958 A1 10/2017 Watanabe et al.

FOREIGN PATENT DOCUMENTS

| JP | 01-232253 A | 9/1989 |
| JP | 2010-256112 A | 11/2010 |
| JP | 2015-072259 A | 4/2015 |
| JP | 2017-187482 A | 10/2017 |
| JP | 2017-223495 A | 12/2017 |

* cited by examiner

GAS SENSOR ELEMENT AND GAS SENSOR

CROSS-REFERENCE TO RELATED PATENT APPLICATIONS

This application is a U.S. National Phase Application under 35 U.S.C. § 371 of International Patent Application No. PCT/JP2019/027679 filed on Jul. 12, 2019 and claims the benefit of priority to Japanese Patent Application No. 2018-246600 Dec. 28, 2018, the contents of both of which are incorporated herein by reference in their entireties. The International Application was published in Japanese on Jul. 2, 2020 as International Publication No. WO/2020/136962 under PCT Article 21(2).

FIELD OF THE INVENTION

The present invention relates to a gas sensor element and to a gas sensor.

BACKGROUND OF THE INVENTION

A gas sensor for detecting the concentration of a specific gas component in exhaust gas emitted from, for example, the internal combustion engine of an automobile is a known art. Generally, such a gas sensor includes a solid electrolyte layer and further includes a reference electrode and a detection electrode disposed on respective surfaces of the solid electrolyte layer. A reference gas (for example, air) is supplied to the reference electrode, and a gas to be measured (hereinafter referred to as "gas under measurement") is supplied to the detection electrode.

The exhaust gas contains mixture components such as carbon monoxide (CO), nitrogen oxides (NOx), hydrocarbons (HC), and hydrogen ($H_2$). When the mixture components are present, the amount of oxygen consumed during combustion differs from that during complete combustion, so that the detection accuracy of the gas sensor deteriorates. The detection accuracy of the gas sensor can be increased by bringing the exhaust gas into contact with catalysts before the exhaust gas reaches the detection electrode to oxidize or reduce the mixture components to thereby purify the exhaust gas. Generally, noble metals are used as catalyst metals included in catalyst layers. Different noble metals have different catalytic functions. Therefore, in one previously proposed technique, to control the characteristics of a catalyst layer, a combination of a plurality of noble metals is used to form the catalyst layer (see, for example, Japanese Patent Application Laid-Open (kokai) No. 2010-256112).

PRIOR ART DOCUMENTS

Patent Documents

Patent Document 1: Japanese Patent Application Laid-Open (kokai) No. 2010-256112
Patent Document 2: Japanese Patent Application Laid-Open (kokai) No. 2017-223495

Problems to be Solved by the Invention

However, when a plurality of noble metals are supported on one catalyst layer, the plurality of noble metals present in the catalyst layer may form an alloy during production of a gas sensor or during use of the gas sensor. When the noble metals form an alloy, the characteristics of the noble metals as catalysts may change from those before alloying, and therefore the desired catalytic characteristics obtained by combining the plurality of noble metals may not be obtained. The inventor of the present invention has conducted studies and obtained the following findings. When catalyst metals (such as Pt and Pd) that facilitate oxidation reactions of CO and HC form an alloy, influences on the catalytic characteristics are relatively small. However, when a catalyst metal (such as Rh, Ru, or Ir) that facilitates reduction reactions of NOx forms an alloy with a catalyst metals such as Pt or Pd that facilitates the oxidation reactions, the NOx reduction effect decreases significantly.

When different noble metals are supported on catalyst layers adjacent to each other, no alloying occurs within each catalyst layer, but alloying may occur at the interface between the adjacent catalyst layers.

An object of the present invention is to prevent alloying of catalysts that facilitate the NOx reduction reactions to thereby maintain catalytic characteristics.

SUMMARY OF THE INVENTION

Means for Solving the Problems

The present invention has been made to solve the above problem and can be realized as the following modes.

(1) A gas sensor element of one mode of the present invention includes a solid electrolyte body; a first electrode disposed on a surface of the solid electrolyte body that is to be exposed to the gas under measurement; a second electrode disposed on a surface of the solid electrolyte body; and a protective layer containing a ceramic as a main component and disposed in a path through which the gas under measurement is supplied from the outside of the gas sensor element to the first electrode. The protective layer includes at least a first catalyst layer that supports a first catalyst metal other than a metal facilitating a reduction reaction of nitrogen oxide and a second catalyst layer that supports only a second catalyst metal facilitating the reduction reaction of the nitrogen oxide. The first catalyst layer and the second catalyst layer are arranged in the path in such a manner that the first catalyst layer and the second catalyst layer are not in direct contact with each other.

In the gas sensor element of this mode, the second catalyst layer supports only the second catalyst metal, and the first catalyst layer is not in direct contact with the second catalyst layer. Therefore, alloying of the second catalyst metal facilitating the reduction reaction of the nitrogen oxide with other metal species is prevented, so that the catalytic characteristics of the protective layer can be maintained stably.

(2) In the gas sensor element of the above-described mode, the protective layer may further include an intermediate layer composed only of a ceramic and disposed between the first catalyst layer and the second catalyst layer so as to be in contact with the first catalyst layer and the second catalyst layer.

In the gas sensor element of this mode, since the intermediate layer composed only of the ceramic is present between the first catalyst layer and the second catalyst layer, the alloying can be more preferably prevented.

(3) In the gas sensor element of the above-described mode, the average pore diameter of the intermediate layer may be larger than that of the outer one of the first catalyst layer and the second catalyst layer. In the gas sensor element of this mode, water infiltrating into the outer one of the first and second catalyst layers from the outside of the gas sensor element is unlikely to penetrate into the intermediate layer having a larger average pore diameter. Therefore, the wetting resistance of the gas sensor element is improved.

(4) In the gas sensor element of the above-described mode, a space may be provided between the first catalyst layer and the second catalyst layer.

In the gas sensor element of this mode, the space is present between the first catalyst layer and the second catalyst layer, so that the alloying can be more preferably prevented.

(5) In the gas sensor element of the above-described mode, each of the first catalyst layer and the second catalyst layer may support only one catalyst metal.

In the gas sensor element of this mode, the alloying can be more effectively prevented, and the catalytic characteristics of the protective layer can be maintained more stably.

(6) In the gas sensor element of the above-described mode, the first electrode may be a detection electrode, and the second electrode may be a reference electrode disposed on a surface of the solid electrolyte body that is to be exposed to a reference gas.

In the gas sensor element of this mode, the catalytic characteristics of the protective layer disposed in the path between the outside of the gas sensor element and the detection electrode can be maintained stably, so that the accuracy of detection can be further improved.

(7) In the gas sensor element of the above-described mode, one of the first catalyst layer and the second catalyst layer may be formed so as to be adjacent to an outer surface of the first electrode, wherein the first electrode contains a metal that is the same as the catalyst metal supported on the one of the first and second catalyst layers that is adjacent to the outer surface of the first electrode.

In the gas sensor element of this mode, alloying of the metal in the first electrode with the catalyst metal supported on the first protective layer can be prevented, so that the catalytic characteristics of the protective layer can be maintained more stably.

The present invention can be embodied as, in addition to the above modes, for example, a gas sensor including the gas sensor element, a method for producing the gas sensor element, a method for producing the gas sensor, a protective layer for the gas sensor element, a method for forming the protective layer for the gas sensor element, etc.

DETAILED DESCRIPTION OF THE INVENTION

A. First Embodiment

A-1. Structure of Gas Sensor

Figure 1:
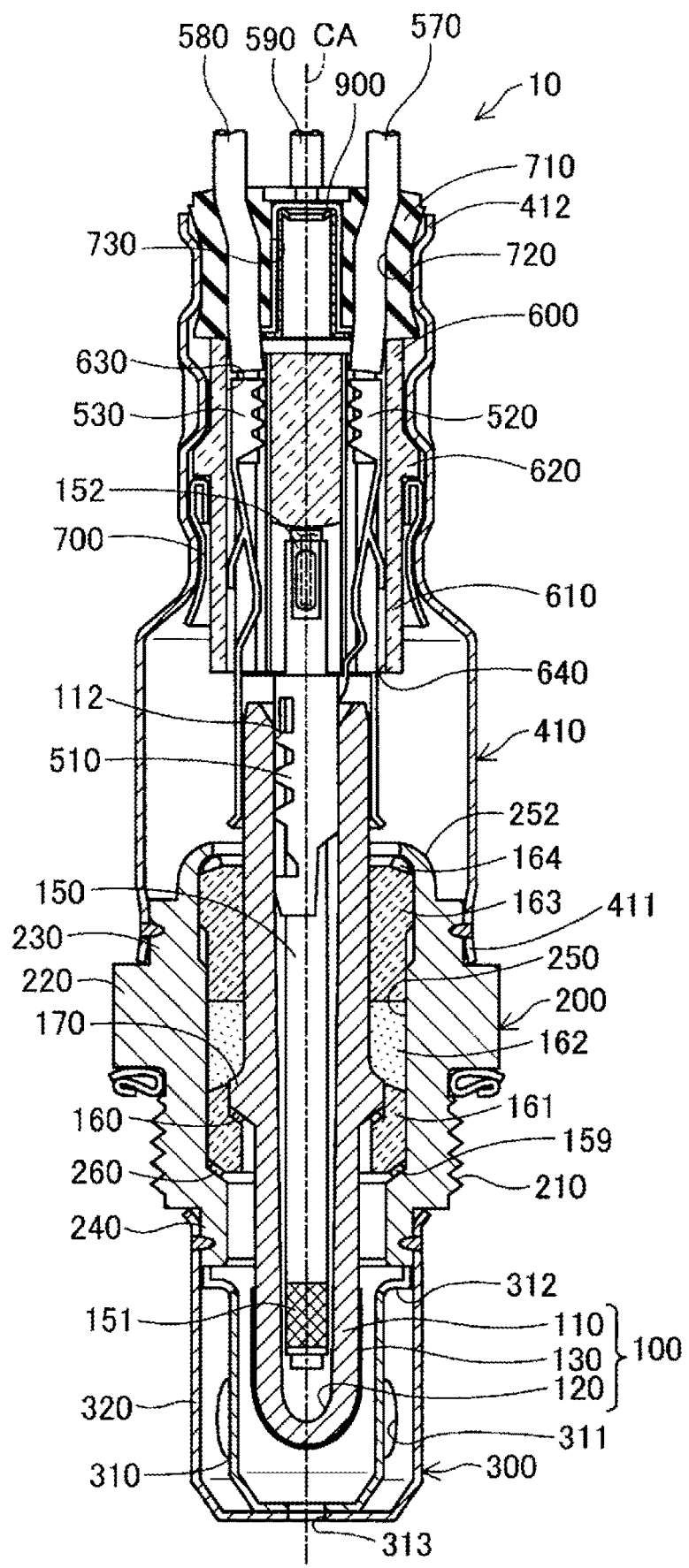
FIG. 1 is a cross-sectional view showing the structure of a gas sensor according to a first embodiment of the present invention.

FIG. 1 is a cross-sectional view showing the structure of a gas sensor 10 serving as a first embodiment of the present invention. The gas sensor 10 is fixed to an exhaust pipe of an unillustrated internal combustion engine (engine) and measures the concentration of a specific gas contained in the exhaust gas which is a gas under measurement. Examples of the specific gas include oxygen and NOx, and the gas sensor 10 of the present embodiment measures the concentration of oxygen gas.

FIG. 1 shows a cross section of the gas sensor 10 in the direction of an axial line CA. The axial line CA extends in the longitudinal direction of the gas sensor 10 at the center of the gas sensor 10. In the following description, the lower side in the drawing sheet of FIG. 1 is referred to as a "forward end side," and the upper side is referred to as a "rear end side." A direction passing through the axial line CA and perpendicular to the axial line CA is referred to as a "radial direction."

The gas sensor 10 mainly includes a sensor element 100, a metallic shell 200, a protector 300, a ceramic heater 150, an outer casing 410, a separator 600, and a grommet 710.

The sensor element 100 outputs a signal for detecting the concentration of oxygen in the exhaust gas. The sensor element 100 is formed into the shape of a tube with a closed forward end and has a bore 112 which is open at the rear end. The sensor element 100 mainly includes a solid electrolyte body 110, a reference electrode 120 formed on the inner surface of the solid electrolyte body 110, and a detection electrode 130 formed on the outer surface of the solid electrolyte body 110. The structures of these components will be described later. The sensor element 100 is fixed inside the metallic shell 200. A forward end portion of the sensor element 100 protrudes from the forward end of the metallic shell 200, and the exhaust gas is supplied to the forward end portion. A rear end portion of the sensor element 100 protrudes from the rear end of the metallic shell 200, and a connection terminal 510 is inserted into the bore 112 of the sensor element 100. A flange portion 170 protruding radially outward is provided at approximately the center of the sensor element 100. In the present embodiment, the "sensor element 100" function as a "gas sensor element."

The metallic shell 200 is a tubular metal member that surrounds and holds the circumference of the sensor element 100 and is used to attach the gas sensor 10 to the exhaust pipe. The metallic shell 200 in the present embodiment is formed of SUS430.

A forward end portion 240, a threaded portion 210, a flange portion 220, a rear end portion 230, and a crimp portion 252 are formed on the outer circumference of the metallic shell 200 in the above order from the forward end side. The forward end portion 240 is a portion formed on the forward end side of the metallic shell 200 such that the metallic shell 200 has a reduced outer diameter. The metallic shell 200 and the protector 300 are joined together with the forward end portion 240 of the metallic shell 200 inserted into the protector 300. The threaded portion 210 is a male thread formed for screwing the gas sensor 10 into the exhaust pipe for attachment of the gas sensor 10. The flange portion 220 is a portion formed such that the outer diameter of the metallic shell 200 protrudes radially outward so as to form a polygonal shape. The flange portion 220 is used for engagement with a tool for attaching the gas sensor 10 to the exhaust pipe. Therefore, the flange portion 220 has a shape (e.g., a hexagonal bolt shape) that allows engagement with the tool. The rear end portion 230 is a portion formed on the rear end side of the metallic shell 200 such that the metallic shell 200 has a reduced outer diameter. The metallic shell 200 and the outer casing 410 are joined together with the rear end portion 230 of the metallic shell 200 inserted into the outer casing 410.

A bore 250 is provided in the metallic shell 200. The bore 250 is a through hole extending through the metallic shell 200 along the axial line CA, and the sensor element 100 is inserted into the bore 250. A step portion 260 is provided on the inner surface of the metallic shell 200 that defines the bore 250 such that the metallic shell 200 is reduced in inner diameter. A ceramic holder 161 is engaged with the step portion 260 through a packing 159. The flange portion 170 of the sensor element 100 is engaged with the ceramic holder 161 through a packing 160. Within the bore 250 of the metallic shell 200, a sealing section 162, a ceramic sleeve 163, and a metal ring 164 are disposed on the rear end side of the ceramic holder 161. The sealing section 162 is a talc layer formed by filling talc powder. The sealing section 162 blocks flow of gas between the forward end side and the rear end side in the direction of the axial line CA through a gap between the sensor element 100 and the metallic shell 200. The ceramic sleeve 163 is a tubular insulating member that surrounds the outer circumference of the sensor element 100. The metal ring 164 is a flat washer that is made of stainless steel and surrounds the outer circumference of the sensor element 100.

Moreover, an opening end of the metallic shell 200 on the rear end side is bent radially inward (toward the bore 250), whereby the crimp portion 252 is formed. The crimp portion 252 presses the sealing section 162 through the metal ring 164 and the ceramic sleeve 163, and the sensor element 100 is thereby fixed inside the metallic shell 200.

The protector 300 is a closed-end cylindrical metal member for protecting the sensor element 100. The protector 300 is fixed to the forward end portion 240 by laser welding so as to surround the sensor element 100 protruding from the forward end of the metallic shell 200. The protector 300 is a double protector including an inner protector 310 and an outer protector 320. Gas introduction holes 311 and 312 and gas discharge holes 313 are formed in the inner protector 310 and the outer protector 320. The gas introduction holes 311 and 312 are through holes formed for introducing the exhaust gas into the interior of the protector 300 (into the sensor element 100). The gas discharge holes 313 are through holes formed for discharging the exhaust gas from the interior of the protector 300 to the outside.

The ceramic heater 150 heats the sensor element 100 to a prescribed activation temperature to increase the oxygen ion conductivity of the solid electrolyte body 110 to thereby stabilize the operation of the sensor element 100. The ceramic heater 150 is disposed inside the bore 112 of the sensor element 100. The ceramic heater 150 includes a heat generating portion 151 and heater connection terminals 152. The heat generating portion 151 is a heat generating resistor formed of a conductor such as tungsten and generates heat when electric power is supplied thereto. The heater connection terminals 152 are disposed on the rear end side of the ceramic heater 150 and are connected to heater lead wires 590. The heater connection terminals 152 receive electric power from the outside through the heater lead wires 590. Notably, the gas sensor 10 may be a heater-less gas sensor that does not have the ceramic heater 150.

The outer casing 410 is a cylindrical metal member having a through hole along the axial line CA. The rear end portion 230 of the metallic shell 200 is inserted into a forward end portion 411 of the outer casing 410. The outer casing 410 and the metallic shell 200 are joined together by laser welding. The grommet 710 described later is fitted into a rear end portion 412 of the outer casing 410. The grommet 710 is fixed to the outer casing 410 by crimping the rear end portion 412 of the outer casing 410.

The separator 600 is a member made of an insulating member such as alumina and formed into an approximately cylindrical shape and is disposed inside the outer casing 410. A separator body 610 and a separator flange portion 620 are formed in the separator 600. Lead wire insertion holes 630 extending through the separator 600 along the axial line CA and a holding hole 640 having an opening on the forward end side of the separator 600 are formed in the separator body 610. Element lead wires 570 and 580 described later and the heater lead wires 590 are inserted into the lead wire insertion holes 630 from their rear end side. A rear end portion of the ceramic heater 150 is inserted into the holding hole 640. The rear end surface of the inserted ceramic heater 150 abuts against the bottom surface of the holding hole 640, and the position of the ceramic heater 150 in the direction of the axial line CA is thereby determined. The separator flange portion 620 is a portion formed on the rear end side of the separator 600 such that the separator 600 is increased in outer diameter. The separator flange portion 620 is supported by a holding member 700 disposed in the gap between the outer casing 410 and the separator 600, and the separator 600 is thereby fixed inside the outer casing 410.

The grommet 710 is made of, for example, fluorocarbon rubber having good heat resistance and is fitted into the rear end portion 412 of the outer casing 410. The grommet 710 has formed therein a through hole 730 extending through a central portion of the grommet 710 along the axial line CA and four lead wire insertion holes 720 passing though the grommet 710 along the axial line CA so as to surround the through hole 730. A filter unit 900 (a filter and a metal tube) that closes the through hole 730 is disposed in the through hole 730.

The element lead wires 570 and 580 and the heater lead wires 590 are each formed from a conductor coated with a resin-made insulating coating. Rear end portions of the conductors of the element lead wires 570 and 580 and the heater lead wires 590 are electrically connected to connector terminals provided in a connector. A forward end portion of the conductor of the element lead wire 570 is crimped and connected to a rear end portion of the inner connection terminal 520 fitted into a rear end portion of the sensor element 100. The inner connection terminal 520 is a conductor that electrically connects the element lead wire 570 to the reference electrode 120 of the sensor element 100. A forward end portion of the conductor of the element lead wire 580 is crimped and connected to a rear end portion of the outer connection terminal 530 fitted onto the rear end portion of the sensor element 100. The outer connection terminal 530 is a conductor that electrically connects the element lead wire 580 to the detection electrode 130 of the sensor element 100. Forward end portions of the conductors of the heater lead wires 590 are electrically connected to the heater connection terminals 152 of the ceramic heater 150. The element lead wires 570 and 580 and the heater lead wires 590 are inserted into the respective lead wire insertion holes 630 of the separator 600 and the respective lead wire insertion holes 720 of the grommet 710 and extend from the inner side of the outer casing 410 to the outside.

In the above-described gas sensor 10 of the present embodiment, air is introduced from the through hole 730 of the grommet 710 into the interior of the outer casing 410 through the filter unit 900, and the air is thereby introduced into the bore 112 of the sensor element 100. The air introduced into the bore 112 of the sensor element 100 is used as a reference gas that serves as a reference when the gas sensor 10 (the sensor element 100) detects oxygen in the exhaust gas. The gas sensor 10 of the present embodiment is configured such that the exhaust gas (gas under measurement) is introduced into the interior of the protector 300 through the gas introduction holes 311 and 312 of the protector 300 so that the sensor element 100 is exposed to the exhaust gas. As a result, an electromotive force corresponding to the difference in oxygen concentration between the reference gas and the exhaust gas (gas under measurement) is generated in the sensor element 100. The electromotive force of the sensor element 100 is outputted as a sensor output to the outside of the gas sensor 10 through the element lead wires 570 and 580.

A-2. Structure of Sensor Element

Figure 2:
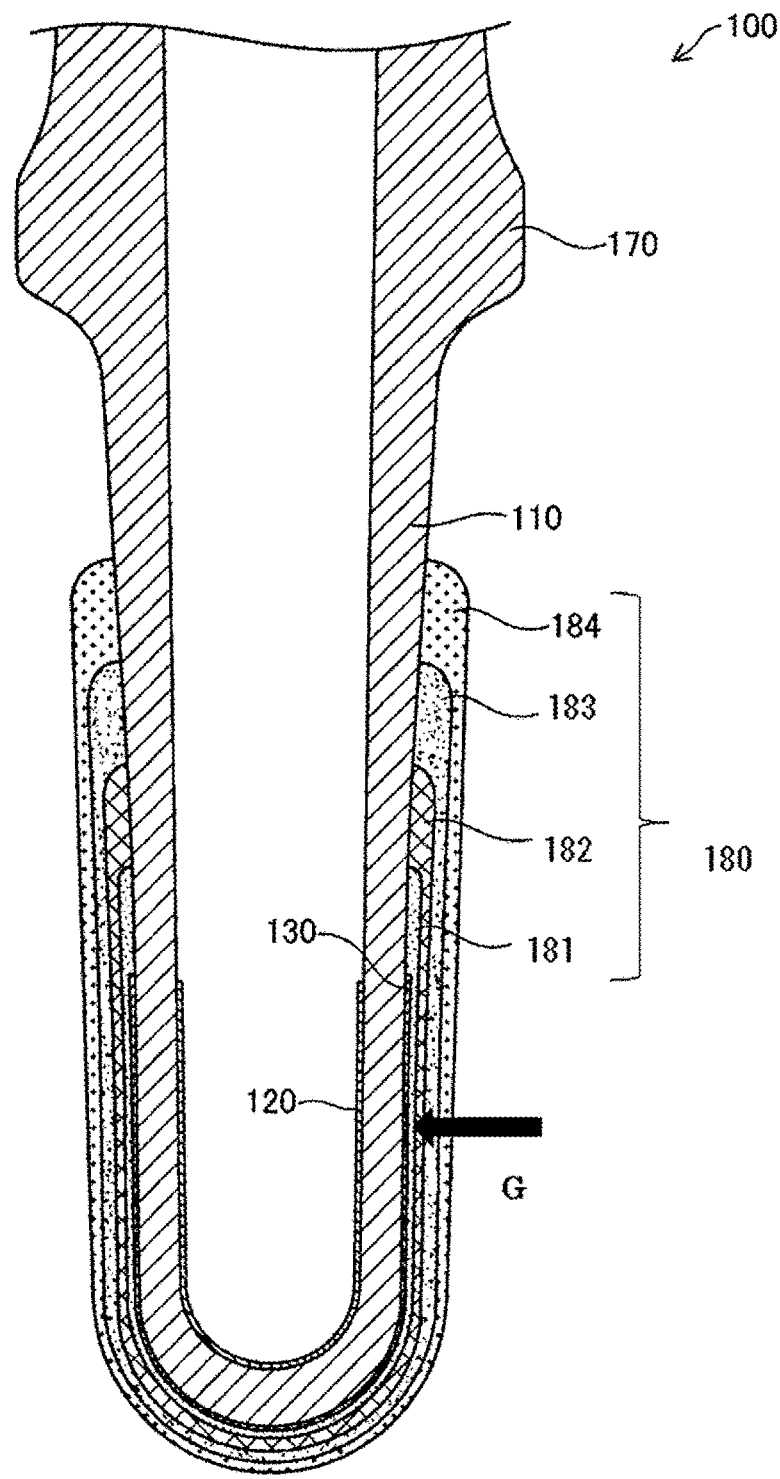
FIG. 2 is a cross-sectional view of a gas sensor element according to the first embodiment of the present invention.

FIG. 2 is a cross-sectional view showing a forward end portion of the sensor element 100. The sensor element 100 of the present embodiment includes the solid electrolyte body 110, the reference electrode 120, the detection electrode 130, and a protective layer 180.

The solid electrolyte body 110, together with the reference electrode 120 and the detection electrode 130, functions as an oxygen concentration cell that detects the concentration of oxygen in the exhaust gas. The solid electrolyte body 110 is formed into a closed-bottom tubular shape extending in the direction of the axial line CA and having a closed forward end. The solid electrolyte body 110 is composed of a solid electrolyte having oxide ion conductivity (oxygen ion conductivity). In the present embodiment, the solid electrolyte body 110 is composed of zirconium oxide ($ZrO_2$) containing yttrium oxide ($Y_2O_3$) as a stabilizer, i.e., yttria-stabilized zirconia (YSZ).

Alternatively, the solid electrolyte body 110 may be composed of another solid electrolyte such as stabilized zirconia containing an oxide added thereto, the oxide being selected from calcium oxide (CaO), magnesium oxide (MgO), cerium oxide ($CeO_2$), scandium oxide ($Sc_2O_3$), etc.

The reference electrode 120 is formed on the inner surface of the solid electrolyte body 110 to which the air (the reference gas) is supplied and is exposed to the reference gas. The detection electrode 130 is formed on the outer surface of the solid electrolyte body 110 to which the exhaust gas (the gas under measurement) is supplied and is exposed to the gas under measurement. Preferably, the reference electrode 120 and the detection electrode 130 are formed of a noble metal or a noble metal alloy such as platinum (Pt) or a platinum alloy. In the present embodiment, the reference electrode 120 and the detection electrode 130 are formed of Pt, and zirconium oxide is added thereto.

The protective layer 180 includes a first catalyst layer 181, an intermediate layer 182, a second catalyst layer 183, and an outermost layer 184, and these layers are porous layers. The first catalyst layer 181 is formed on the outer surface of the solid electrolyte body 110 so as to cover the detection electrode 130. The first catalyst layer 181 is a layer formed by thermal-spraying of a ceramic such as spinel. Although the details will be described later, the first catalyst layer 181 supports a first catalyst metal and has the functions of improving adhesion to the intermediate layer 182, protecting the detection electrode 130, etc. The first catalyst layer 181 also functions as a resistance to the flow of the exhaust gas flowing into the detection electrode 130. As a result, the flow of the exhaust gas is diffused uniformly, and the diffused exhaust gas is delivered to the detection electrode 130. The intermediate layer 182 is a porous body composed only of a ceramic such as alumina and supports no catalyst metal. The intermediate layer 182 is formed on the outer surface of the solid electrolyte body 110 so as to cover the entire first catalyst layer 181. The second catalyst layer 183 is a porous body composed of a ceramic such as alumina. Although the details will be described later, the second catalyst layer 183 supports a second catalyst metal and is formed on the outer surface of the solid electrolyte body 110 so as to cover the entire intermediate layer 182. In other words, the first catalyst layer 181 and the second catalyst layer 183 are not in direct contact with each other and are disposed with the intermediate layer 182 interposed therebetween. Notably, the second catalyst layer 183 is not required to cover the entire intermediate layer 182. However, to prevent the mixture components in the exhaust gas from reaching the electrode, it is preferable that the entire detection electrode 130 is covered with the protective layer 180.

Noble metal catalysts are supported on the first catalyst layer 181 and the second catalyst layer 183. Specifically, the first catalyst layer 181 includes a first carrier composed of a ceramic and a first catalyst metal that is a catalyst metal supported on the carrier. The second catalyst layer 183 includes a second carrier composed of a ceramic and a second catalyst metal that is a catalyst metal supported on the carrier.

The first and second carriers are each preferably a porous body formed by aggregating oxide primary particles. From the viewpoint of increasing the specific surface areas of the carriers, it is preferable that the carriers have high durability at high temperature so that no phase transition and no sharp reduction in specific surface area occur in a high temperature atmosphere. In the present embodiment, the first carrier is formed of spinel, and the second carrier is formed of alumina.

The first and second catalyst metals facilitate different reactions of the mixture components (such as HC, CO, NOx, and hydrogen) in the exhaust gas. In the present embodiment, the first catalyst metal used is other than a catalyst metal that facilitates the reduction reactions of NOx and is platinum (Pt) serving as a catalyst that facilitates the oxidation reactions of unburnt components such as HC and CO, and the second catalyst metal used is rhodium (Rh) serving as a catalyst that facilitates the reduction reactions of NOx.

The average pore diameter of the intermediate layer 182 is larger than the average pore diameter of the second catalyst layer 183. Therefore, even when water from the outside adheres to the sensor element 100, penetration of the water into the inner side of the intermediate layer 182 due to capillarity is unlikely to occur, and cracking of the sensor element 100 due to wetting can be prevented.

The outermost layer 184 is a layer that protects the sensor element 100 and covers the entire detection electrode 130 through the first catalyst layer 181, the intermediate layer 182, and the second catalyst layer 183. The outermost layer 184 is formed of, for example, at least one ceramic selected from the group consisting of alumina, titania, spinel, zirconia, mullite, zircon, and cordierite as a main component, and no catalyst metal is supported on the outermost layer 184. Notably, the outermost layer 184 may contain glass and may be omitted.

Notably, the fact that the protective layer 180 provided in the sensor element has the above-described structure including the first catalyst layer 181 and the second catalyst layer 183 can be confirmed, for example, by performing mapping for the noble metals on a cross section including the catalyst layers in the sensor element, through use of an EPMA-WDS (wavelength dispersive X-ray spectrometer) or an EPMA-EDS (energy dispersive X-ray spectrometer).

The detection electrode 130 in the present embodiment corresponds to the first electrode in the claims, and the reference electrode 120 corresponds to the second electrode in the claims.

A-3. Method for Producing Sensor Element

Figure 3:
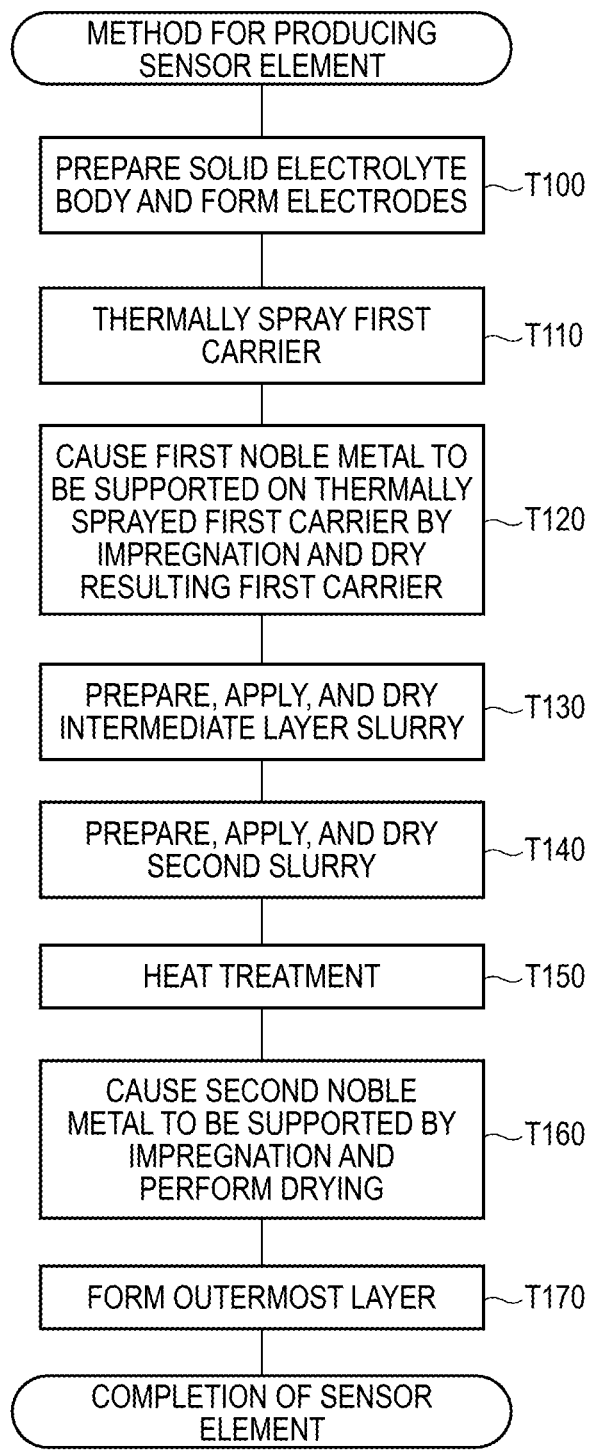
FIG. 3 is a flowchart showing a method for producing the gas sensor element according to the first embodiment of the present invention.

FIG. 3 is a flowchart showing a method for producing the sensor element 100 of the present embodiment. To produce the sensor element 100, first, the solid electrolyte body 110 is prepared, and the reference electrode 120 and the detection electrode 130 are formed on respective surfaces of the prepared solid electrolyte body 110 (step T100). Specifically, the material of the solid electrolyte body 110 (for example, yttria-stabilized zirconia powder) is subjected to pressing and cut into a shape (tubular shape) shown in FIG. 2 to obtain a green workpiece (green compact), and the green compact is fired to obtain the solid electrolyte body 110. Then electroless plating, for example, is used to form the reference electrode 120 and the detection electrode 130 in prescribed positions on the respective surfaces of the solid electrolyte body 110.

Then a ceramic (e.g., spinel) used as the first carrier is thermally sprayed so as to cover the detection electrode 130 to thereby obtain a layer of the first carrier (T110). Notably, a method other than thermal spraying may be used to form the first carrier layer. The first carrier layer may be formed on a surface of the solid electrolyte body 110 using a well-known method including, for example, preparing a slurry of the first carrier and immersing the solid electrolyte body 110 in the slurry.

Then, to form the first catalyst layer 181, the first catalyst metal is caused to be supported on the thermally sprayed first carrier (step T120). In the present embodiment, the solid electrolyte body 110 with the thermally sprayed first carrier is immersed in a solution containing platinum (Pt) serving as the first catalyst metal, specifically an aqueous solution of, for example, chloroplatinic acid or dinitroamine platinum nitrate. Then the resulting solid electrolyte body 110 is dried to cause Pt to be supported on the first carrier. The supporting method is not limited to the above method. For example, the first catalyst layer 181 can also be obtained by the following method. The first catalyst metal is caused to be supported on the first carrier in advance using a well-known method, and a slurry of the first carrier supporting the first catalyst metal is prepared, then applied to the solid electrolyte body in T110, and dried.

Then, to form the intermediate layer 182, an intermediate layer slurry is prepared and dried on the outer surface of the solid electrolyte body 110 (T130). In the present embodiment, the intermediate layer slurry is prepared by adding a pore-forming agent (such as carbon) and a binder to alumina powder. The prepared intermediate layer slurry is applied to the outer surface of the solid electrolyte body 110 so as to cover the precursor layer for the first catalyst layer 181 formed in step T120 and then dried.

To form the second catalyst layer 183, a second slurry is prepared, applied to the precursor layer for the intermediate layer 182 on the outer surface of the solid electrolyte body 110, and then dried (step T140). Specifically, the second slurry is prepared by adding a pore-forming agent (such as carbon) and a binder to alumina powder serving as the second carrier. In the present embodiment, the particle diameter of the pore-forming agent added to the second slurry is larger than the particle diameter of the pore-forming agent added to the intermediate layer slurry. Specifically, the average pore diameter of the intermediate layer 182 after heat treatment described later is larger than the average pore diameter of the second catalyst layer 183.

After the drying, the solid electrolyte body 110 including formed therein the precursor layer for the first catalyst layer 181, the precursor layer for the intermediate layer 182, and the second slurry layer is subjected to heat treatment (step T150) to form the first catalyst layer 181, the intermediate layer 182, and a precursor layer for the second catalyst layer 183. The heat treatment (step 150) is performed for the purpose of burning out the binder components in the slurries, thermally decomposing the supported noble metal complex to obtain the noble metal, etc. In the heat treatment, a heating furnace, for example, is used, and the temperature of the atmosphere inside the heating furnace may be set to 1000° C.

A solution containing rhodium (Rh) serving as the second catalyst metal, specifically, a solution of a water-soluble salt such as rhodium chloride, rhodium nitrate, or rhodium oxide hydrate (i.e., rhodium hydroxide) is prepared, and the solid electrolyte body 110 is immersed in the prepared solution and dried to cause the second catalyst metal to be supported on the precursor layer for the second catalyst layer 183 (step T160). In the present embodiment, since the average pore diameter of the intermediate layer 182 is larger than the average pore diameter of the second catalyst layer 183 as described above, penetration of the aqueous solution containing Rh into the intermediate layer 182 due to capillarity is prevented. Therefore, the intermediate layer 182 is not impregnated with Rh even when the impregnation conditions such as immersion time are not controlled precisely, and only the second catalyst layer 183 is impregnated with Rh. Of course, even when the relation between the pore diameter of the intermediate layer 182 and the pore diameter of the second catalyst layer 183 differs from the relation in the present embodiment, only the second catalyst layer 183 can be impregnated with Rh by appropriately adjusting the temperature of the solution, its concentration, the immersion time, etc.

The supporting method is not limited to the above method. For example, a second slurry containing the second catalyst metal may be prepared. Then the second slurry containing the second catalyst metal may be applied to the solid electrolyte 110 and then dried.

Then the outermost layer 184 is formed on the outer surface of the solid electrolyte body 110 so as to cover the second catalyst layer 183 (step T170). The protective layer 180 is thereby obtained, and the sensor element 100 is completed. To form the outermost layer 184, first, a material for the protective layer containing a ceramic as a main component is applied to the second catalyst layer 183 and then subjected to heat treatment.

A-4. Effects of Present Embodiment

In the gas sensor 10 of the present embodiment configured as described above, the first catalyst layer 181 and the second catalyst layer 182 are formed so as to cover the detection electrode 130. The first catalyst layer 181 supports only platinum (Pt) that is a catalyst metal other than a catalyst facilitating the NOx reduction reactions and facilitates the oxidation reactions of hydrogen, HC, etc. The second catalyst layer 183 supports only rhodium (Rh) facilitating the NOx reduction reactions. Therefore, the exhaust gas reaching the outer surface of the sensor element 100 from the outside of the sensor element 100 passes through the protective layer 180 in the order of the outermost layer 184, the second catalyst layer 183, the intermediate layer 182, and the first catalyst layer 181 as shown by, for example, a path G in FIG. 2 and then reaches the detection electrode 130. During passage of the exhaust gas through the second catalyst layer 183, NOx is reduced while the reduction is catalyzed by Rh. During passage of the resulting exhaust gas through the first catalyst layer 181, unburnt components such as hydrogen, HC, and CO are oxidized while the oxidation is catalyzed by Pt. Then the exhaust gas with the mixture components removed reaches the detection electrode 130. Therefore, the detection accuracy of the gas sensor is increased.

The first catalyst layer 181 supports only Pt, and the second catalyst layer 183 supports only Rh. Therefore, the catalytic action of Pt facilitates the oxidation reactions of the unburnt components in the exhaust gas, and the catalytic action of Rh facilitates the reduction reactions of NOx in the exhaust gas. Moreover, in the course of production and use of the gas sensor, Rh is not alloyed with the other noble metal, and purification catalytic characteristics for the mixture components in the exhaust gas, particularly the catalytic characteristics for the reduction reactions of NOx, are maintained stably. In the present embodiment, the intermediate layer 182 is formed between the first catalyst layer 181 and the second catalyst layer 183, i.e., the first catalyst layer 181 and the second catalyst layer 183 are formed in such a manner that the first catalyst layer 181 and the second catalyst layer 183 are not in contact with each other. Therefore, no alloying occurs at the interface between the first catalyst layer 181 and the second catalyst layer 183, and the purification catalytic characteristics for the mixture components in the exhaust gas, particularly the catalytic characteristics for the NOx reduction reactions, are maintained preferably.

In the gas sensor 10 of the present embodiment, the first catalyst layer 181 supports, as the first catalyst metal, only platinum (Pt) that facilitates the oxidation reactions of hydrogen, HC, etc., and the second catalyst layer 183 supports, as the second catalyst metal, only rhodium (Rh) that facilitates the NOx reduction reactions. Specifically, each of these catalyst layers supports one catalyst metal. This can more preferably prevent alloying, and the catalytic characteristics are maintained.

In the gas sensor 10 of the present embodiment, the noble metal in the detection electrode 130 is composed of Pt, and the first catalyst layer 181 supports Pt. Therefore, no alloying occurs between the detection electrode 130 and the first catalyst layer 181, and the catalytic characteristics can be maintained preferably.

In the gas sensor 10 of the present embodiment, the average pore diameter of the intermediate layer 182 is larger than the average pore diameter of the second catalyst layer 183. Therefore, even when water from the outside adheres to the sensor element 100, penetration of the water into the inner side of the intermediate layer 182 due to capillarity is unlikely to occur, and cracking of the sensor element 100 due to wetting can be prevented.

In the present embodiment, the first catalyst layer 181 supports only Pt, and the second catalyst layer 183 supports only Rh, but a different structure may be used. For example, Pd may be supported instead of Pt. When a change in sensor characteristics due to alloying is permissible, a plurality of noble metals may be used. For example, since both Pt and Pd are noble metals that facilitate the oxidation reactions of unburnt components such as HC and CO, the influence of alloying on the sensor characteristics is relatively small. Therefore, when the influence of alloying is permissible, both Pt and Pd may be supported. Ru or Ir, for example, may be supported instead of Rh. In the present embodiment, the first catalyst layer 181 is formed on the inner side, and the second catalyst layer 183 is formed on the outer side. However, a different structure may be used. For example, the positional relation between the first catalyst layer 181 and the second catalyst layer 183 may be reversed. In this case, it is preferable that the detection electrode 130 and the metal supported on the first catalyst layer 181 are the same metal, but this is not a limitation.

In the present embodiment, one intermediate layer 182 is disposed between the first catalyst layer 181 and the second catalyst layer 183, but a different structure may be used. For example, instead of the intermediate layer 182, two or more layers may be provided. In this case, it is necessary that no noble metal catalyst be supported on layers adjacent to the first catalyst layer 181 and the second catalyst layer 183.

Alternatively, for example, a space may be provided instead of the intermediate layer 182. In this case, the first catalyst layer is spaced apart from second catalyst layer, and the outer one of the first and second catalyst layers is formed, for example, so as to be joined directly to the solid electrolyte body or joined to another member included in the gas sensor. For example, the space is formed by applying, instead of the intermediate layer slurry, a burnable material (such as carbon) paste in step T130 of applying the intermediate layer slurry. In this case, the burnable material burns out during heat treatment, and the space is thereby formed.

B. Second Embodiment

B-1. Structure of Gas Sensor

Figure 4:
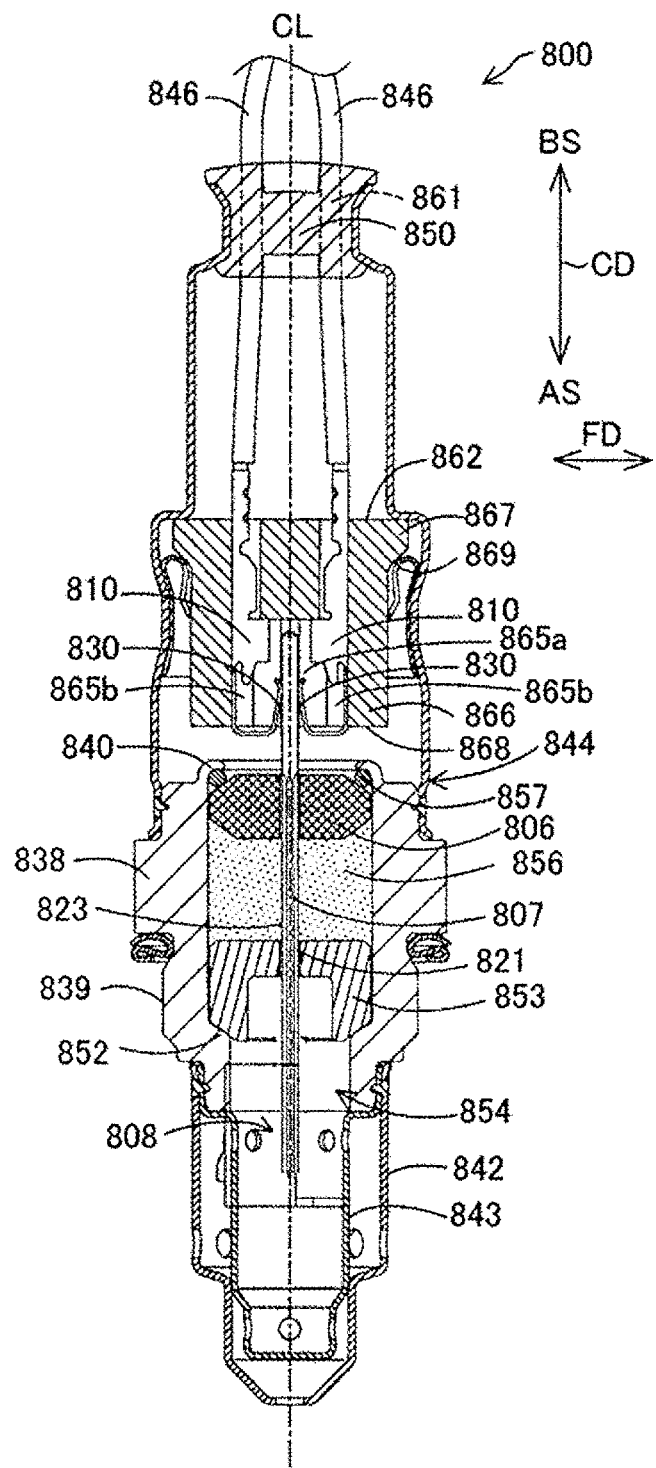
FIG. 4 is a cross-sectional view showing the structure of a gas sensor according to a second embodiment of the present invention.

FIG. 4 is a cross-sectional view showing the structure of a gas sensor 800 of a second embodiment of the present invention. Like the gas sensor 10 of the first embodiment, the gas sensor 800 is a sensor for measuring the concentration of a specific gas contained in exhaust gas used as the gas under measurement. In the present embodiment, the gas sensor 800 measures the concentration of oxygen gas.

FIG. 4 shows a cross section in an axial direction CD. The axial direction CD is a direction parallel to an axial line CL of the gas sensor 800, i.e., the longitudinal direction of the gas sensor 800. In the following description, the lower side in the drawing sheet of FIG. 4 is referred to also as a forward end side AS of the gas sensor 800, and the upper side in the drawing sheet of FIG. 4 is referred to also as a rear end side BS of the gas sensor 800.

The gas sensor 800 includes: a plate-shaped sensor element 807 extending in the axial direction CD; a separator 866 into which the rear end side BS of the sensor element 807 is inserted; metallic terminal members 810 in contact with electrode terminals 830 formed on the rear end side BS of the sensor element 807; and a metallic shell 838 that surrounds the sensor element 807 at a position on the forward end side AS of the separator 866. In the present embodiment, "the sensor element 807" functions as the "gas sensor element." Four electrode terminals 830 and four metallic terminal members 810 are provided. In FIG. 4, only two electrode terminals 830 and two metallic terminal members 810 are illustrated.

The sensor element 807 outputs a signal for detecting the concentration of oxygen in the exhaust gas. The sensor element 807 has a first plate surface 821 forming its principal surface and a second plate surface 823 that is a back surface opposite to the first plate surface 821. The sensor element 807 is formed by stacking a plurality of plate-shaped members as described later. A direction orthogonal to the axial direction CD and also orthogonal to the first plate surface 821 and the second plate surface 823 is referred to as a stacking direction FD. The sensor element 807 includes: a detection portion 808 located on the forward end side AS and exposed to the gas under measurement; and the four electrode terminals 830 located on the rear end side BS and in contact with the respective metallic terminal members 810. Two of the four electrode terminals 830 are formed on the first plate surface 821, and the other two are formed on the second plate surface 823. The sensor element 807 is fixed inside the metallic shell 838 with the detection portion 808 of the sensor element 807 protruding from the forward end of the metallic shell 838 and the electrode terminals 830 protruding from the rear end of the metallic shell 838. The details of the sensor element 807 will be described later.

The separator 866 is formed from an insulating member such as alumina. The separator 866 has an approximately tubular shape. The separator 866 is disposed so as to surround a rear end side portion of the sensor element 807 in which the electrode terminals 830 are positioned. The separator 866 has an insertion portion 865*a* into which the rear end side portion of the sensor element 807 is inserted and four grooves 865*b* (only two grooves are illustrated in the figure) formed on the inner wall surface of the insertion portion 865*a*. The four grooves 865*b* extend in the axial direction CD through the separator 866 from its forward-end-side end face 868 to its rear-end-side end face 862. Each of the metallic terminal members 810 is inserted into a corresponding one of the four grooves 865*b*. The separator 866 has a flange portion 867 disposed on the rear end side BS and protruding radially outward.

The metallic terminal members 810 inserted into the respective grooves 865*b* are disposed so as to be located between the sensor element 807 and the separator 866 in the stacking direction FD. The metallic terminal members 810 are sandwiched between the sensor element 807 and the separator 866. The metallic terminal members 810 form current paths between the sensor element 807 and an external device for computing the oxygen concentration. The metallic terminal members 810 are electrically connected to lead wires 846 disposed so as to extend from the outside of the gas sensor 800 to the inside and also electrically connected to the electrode terminals 830 of the sensor element 807. Four lead wires 846 corresponding to the four electrode terminals 830 are provided and electrically connected to the external device (only two are illustrated in the figure).

The metallic shell 838 is an approximately tubular metallic member. The metallic shell 838 has a through hole 854 passing therethrough in the axial direction CD and a ledge 852 protruding toward a radially inward region of the through hole 854. The metallic shell 838 holds the sensor element 807 within the through hole 854 such that the detection portion 808 is located on the forward end side AS of the through hole 854 and the electrode terminals 830 are located on the rear end side BS of the through hole 854. The ledge 852 is formed as an inwardly tapered surface inclined with respect to a plane perpendicular to the axial direction CD. A threaded portion 839 for fixing the gas sensor 800 to an exhaust pipe is formed on the outer surface of the metallic shell 838.

An annular ceramic holder 853, a talc ring 856, and a ceramic sleeve 806 are stacked inside the through hole 854 in this order from the forward end side AS to the rear end side BS so as to surround the outer circumference of the sensor element 807. A crimp packing 857 is disposed between the ceramic sleeve 806 and a rear end portion 840 of the metallic shell 838. The rear end portion 840 of the metallic shell 838 is crimped such that the ceramic sleeve 806 is pressed toward the forward end side AS through the crimp packing 857.

The gas sensor 800 further includes: an outer casing 844 fixed to the outer circumference of the metallic shell 838 on the rear end side BS; a holding member 869 for holding the separator 866; a grommet 850 disposed on the rear end side BS of the outer casing 844; and outer and inner protectors 842 and 843 fixed to the outer circumference of the metallic shell 838 on the forward end side AS.

The outer casing 844 is an approximately tubular metallic member. The outer circumference of the outer casing 844 is attached on its forward end side AS to the metallic shell 838 by, for example, laser welding. The outer casing 844 is reduced in outer diameter on the rear end side BS, and the grommet 850 is fitted into an opening of the diameter-reduced portion of the outer casing 844. Four lead wire insertion holes 861 (only two are illustrated in FIG. 4) for insertion of the lead wires 846 are formed in the grommet 850.

The holding member 869 is an approximately tubular metallic member. The holding member 869 is fixed to the outer casing 844 and positioned within the outer casing 844. The flange portion 867 of the separator 866 abuts against the holding member 869 on its rear end side BS, and the separator 866 is thereby held by the holding member 869.

The outer protector 842 and the inner protector 843 are closed-bottom tubular metallic members having a plurality of holes. The outer protector 842 and the inner protector 843 are attached to the outer circumference of the metallic shell 838 on its forward end side AS by, for example, laser welding. The outer protector 842 and the inner protector 843 cover the detection portion 808 to thereby protect the sensor element 807. The gas under measurement passes through the plurality of holes formed in the outer protector 842 and the inner protector 843 and flows into the interior of the inner protector 843.

B-2. Structure of Gas Sensor Element

Figure 5:
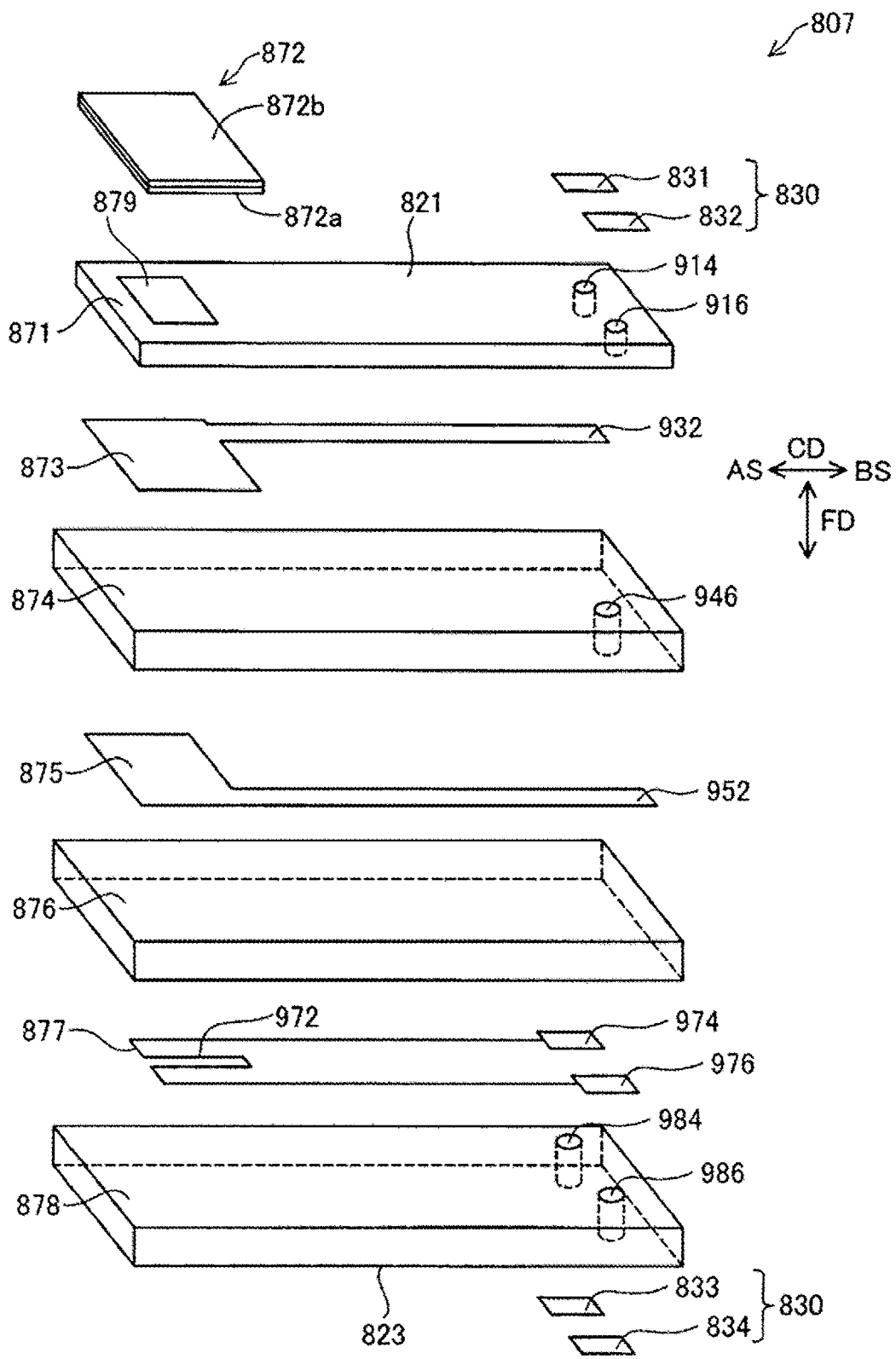
FIG. 5 is an exploded perspective view of a gas sensor element according to the second embodiment of the present invention.

FIG. 5 is an exploded perspective view of the sensor element 807. The axial direction CD, the stacking direction FD, the forward end side AS, and the rear end side BS shown in FIG. 8 correspond to those in FIG. 7. The sensor element 807 includes a catalyst portion 872, an insulating layer 871, a detection electrode 873, a solid electrolyte body 874, a reference electrode 875, an insulating layer 876, a heater 877, and an insulating layer 878. These components are stacked in this order in the stacking direction FD.

In FIG. 5, the four electrode terminals 830 (specifically, electrode terminals 831 to 834) are also illustrated. The electrode terminals 830 are used for electrician connection of the sensor element 807. Each of the electrode terminals 830 is formed using, for example, platinum or rhodium and has an approximately rectangular surface. The electrode terminals 830 can be formed by, for example, screen-printing using a paste composed of platinum as a main component. The electrode terminals 831 and 832 are formed on the first plate surface 821 of the insulating layer 871 so as to be arranged in a direction perpendicular to the axial direction CD on the rear end side BS of the sensor element 807. The electrode terminals 833 and 834 are formed on the second plate surface 823 of the insulating layer 878 so as to be arranged in the direction perpendicular to the axial direction CD on the rear end side BS of the sensor element 807.

The insulating layers 871, 876, and 878 electrically insulate the above layers from one another. The insulating layer 871 functions also as a protective layer for protecting the detection electrode 873. The insulating layers 871, 876, and 878 are rectangular sheet members formed of alumina as a main component. A rectangular hole extending through the insulating layer 871 in the stacking direction FD is formed on the forward end side AS of the insulating layer 871, and a porous layer 879 is formed in this hole. The porous layer 879 is provided in order to diffuse the exhaust gas flowing to the detection electrode 873. The porous layer 879 is composed of a catalyst in which platinum (Pt) is dispersed in and supported on alumina serving as a carrier. The porous layer 879 has the function of purifying the mixture components in the exhaust gas before the exhaust gas reaches the detection electrode 873. In the sensor element 807, a portion including the porous layer 879 on the forward end side AS is included in the detection portion 808 described above. Two through holes 914 and 916 extending through the insulating layer 871 in the stacking direction FD are formed on the rear end side BS of the insulating layer 871. Similarly, two through holes 984 and 986 extending through the insulating layer 878 in the stacking direction FD are formed on the rear end side BS of the insulating layer 878.

The surface protecting portion 872 is formed into an approximately rectangular shape, disposed on the first plate surface 821 of the insulating layer 871 so as to cover the entire porous layer 879, and has the function of purifying the mixture components in the exhaust gas before the exhaust gas reaches the detection electrode 873. The surface protecting portion 872 includes an intermediate layer 872*a* disposed on the side in contact with the insulating layer 871 and a second catalyst layer 872*b* disposed on the side spaced apart from the insulating layer 871. The intermediate layer 872*a* is a porous body formed of alumina, as is the intermediate layer 181 in the first embodiment. The second catalyst layer 872*b* has the same structure as that of the second catalyst layer 183 in the first embodiment. Specifically, the second catalyst layer 872*b* is composed of a catalyst in which rhodium (Rh) used as a second catalyst metal is dispersed in and supported on alumina powder used as a second carrier.

The porous layer 879 can be formed, for example, by causing a first catalyst metal to be supported on a first carrier using a well-known method to thereby prepare a first slurry and then filling a through hole formed in the insulating layer 871 with the first slurry. The intermediate layer 872*a* can be formed by preparing an intermediate layer slurry containing alumina and a pore-forming agent and applying the intermediate layer slurry so as to cover the first slurry layer. The second catalyst layer 872*b* can be formed by causing the second catalyst metal to be supported on the second carrier to thereby prepare a second slurry and then applying the second slurry to the layer of the intermediate layer paste, as in the first embodiment. The layers formed by applying the first slurry, the intermediate layer slurry, and the second slurry can be converted to the porous layer 879, the intermediate layer 872*a*, and the second catalyst layer 872*b*, respectively, by, for example, stacking the components of the sensor element 807, including the insulating layers 871, 876, and 878, and subjecting the entire stack to heat treatment.

The methods of producing the porous layer 879 and the second catalyst layer 872*b* are not limited to the above methods. For example, the porous layer 879 may be obtained as follows. After a layer composed only of the first carrier is formed on the surface of the solid electrolyte body 874, a solution of the first catalyst metal is applied to the first carrier layer to impregnate the first carrier layer with the first catalyst metal. The second catalyst layer 872*b* may be obtained as follows. After a layer composed only of the second carrier is formed on the surface of the solid electrolyte body 874, the solid electrolyte body 874 is immersed in a solution of the second catalyst metal to impregnate the second carrier with the solution.

The solid electrolyte body 874, together with the detection electrode 873 and the reference electrode 875, functions as an oxygen concentration cell for detecting the concentration of oxygen in the exhaust gas. The solid electrolyte body 874 is a rectangular sheet-shaped member and is formed of a solid electrolyte that has oxide ion conductivity (oxygen ion conductivity) and is the same as the constituent material of the solid electrolyte body 110 in the first embodiment. A through hole 946 extending through the solid electrolyte body 874 in the stacking direction FD is formed on the rear end side BS of the solid electrolyte body 874.

The detection electrode 873 is formed using, for example, platinum or rhodium. In the present embodiment, the detection electrode 873 is formed of platinum and zirconium oxide. The detection electrode 873 is disposed on the surface of the solid electrolyte body 874 located on one side in the stacking direction FD (the surface on which the insulating layer 871 is disposed) and is formed so as to overlap the entire porous layer 879 when projected in the stacking direction FD. The detection electrode 873 includes a detection lead portion 932 extending toward the rear end side BS. The detection lead portion 932 of the detection electrode 873 is electrically connected to the electrode terminal 831 through the through hole 914 of the insulating layer 871.

The reference electrode 875 is formed using, for example, platinum or rhodium. The reference electrode 875 is disposed on the surface of the solid electrolyte body 874 located on the other side in the stacking direction FD (the surface on which the insulating layer 876 is disposed) and is formed so as to overlap the entire porous layer 879 when projected in the stacking direction FD. The reference electrode 875 includes a detection lead portion 952 extending toward the rear end side BS. The detection lead portion 952 of the reference electrode 875 is electrically connected to the electrode terminal 832 through the through hole 946 of the solid electrolyte body 874 and the through hole 916 of the insulating layer 871.

A minute current flows between the detection electrode 873 and the reference electrode 875, and oxygen is pumped from the detection electrode 873 to the reference electrode 875. This structure makes it possible to maintain the concentration of oxygen at the reference electrode 875 at a constant level, and output a detection signal which varies depending on a change in concentration of oxygen in the gas under measurement in contact with the detection electrode 873, while using the concentration of oxygen at the reference electrode 875 as the reference.

The heater 877 heats the sensor element 807 to a prescribed activation temperature to increase the oxygen ion conductivity of the solid electrolyte body 874 to thereby stabilize the operation of the gas sensor 800. The heater 877 is a heat-generating resistor formed of a conductor such as platinum and generates heat when electric power is supplied thereto. The heater 877 is held between the insulating layer 876 and the insulating layer 878. A heat generating portion 972 is provided on the forward end side AS of the heater 877. The heat generating portion 972 includes a heat generating wire disposed in a meandering manner and generates heat when energized. The heater 877 includes electrode terminals 974 and 976 on its rear end side BS. The electrode terminals 974 and 976 are electrically connected to the electrode terminals 833 and 834 through the through holes 984 and 986 of the insulating layer 878.

In the gas sensor 800 of the second embodiment configured as described above, the exhaust gas passes from the outside of the sensor element 807 through a path including the second catalyst layer 872b, the intermediate layer 872a, and the porous layer 879 and then reaches the detection electrode 873. The porous layer 879 supports platinum, and the second catalyst layer 872b supports rhodium and is formed so as not be in contact with the porous layer 879. Therefore, the same effects as those of the gas sensor 10 of the first embodiment are obtained. Various modifications can be made to the combination of the first carrier and the first catalyst metal forming the porous layer 879 and the combination of the second carrier and the second catalyst metal forming the second catalyst layer 872b, as in the first embodiment.

In the present embodiment, the detection electrode 873 corresponds to the first electrode in the claims, and the reference electrode 875 corresponds to the second electrode in the claims. The porous layer 879 and the surface protecting portion 872 correspond to the protective layer in the claims, and the porous layer 879 corresponds to the first catalyst layer in the claims.

In the present embodiment also, the same effects as those in the first embodiment can be obtained.

In the present embodiment, the porous layer 879 and the second catalyst layer 872b, which are layers supporting the respective catalysts, cover only the detection electrode 873 and do not cover the reference electrode 875. However, a different structure may be used. For example, a plurality of protective layers covering the entire detection portion 808 may be provided such that a layer supporting the first catalyst metal and a layer supporting the second catalyst metal are not in contact with each other.

In the present embodiment, the porous layer 879, the intermediate layer 872a, and the second catalyst layer 872b are stacked on the detection electrode in this order in the stacking direction, but this structure is not a limitation. For example, the second catalyst metal may be supported on the porous layer 879, and a first catalyst layer supporting the first catalyst metal may be formed instead of the second catalyst layer 872b. Alternatively, for example, the porous layer 879 may support no catalyst metal, and the surface protecting portion 872 may have the first catalyst layer, the intermediate layer, and the second catalyst layer such that the first catalyst layer and the second catalyst layer are not in direct contact with each other.

In the present embodiment, the intermediate layer 872a is formed between the porous layer 879 and the second catalyst layer 872b. However, a different structure may be used. For example, part or all of the intermediate layer 872a may be replaced by a space. In this case, for example, a burnable material (such as carbon) paste is applied instead of the intermediate layer slurry. The burnable material burns out during heat treatment, and the space is thereby formed.

In the present embodiment, the gas sensor element is of the so-called one cell type including only one pair of electrodes, i.e., the detection electrode 873 and the reference electrode 875. However, a different structure may be used. For example, the gas sensor may be of the so-called two-cell type or the so-called three-cell type including additional electrodes in addition to the detection electrode 873 and the reference electrode 875.

In the present embodiment, the detection electrode 873 and the reference electrode 875 correspond to the first electrode and the second electrode, respectively. However, different electrodes may be used so long as at least one of the electrodes is exposed to the gas under measurement. For example, the present invention can be applied to a gas sensor element including a pair of pump electrodes for pumping oxygen between the gas under measurement present outside the gas sensor element and a measurement chamber inside the gas sensor element. In this case, the pair of pump electrodes are regarded as the first electrode and the second electrode.

The present invention is not limited to the above-described embodiments, examples, and modifications and may be embodied in various other forms without departing from the spirit of the invention. For example, the technical features in the embodiments, examples, and modifications corresponding to the technical features in the modes described in SUMMARY OF THE INVENTION can be appropriately replaced or combined to solve some of or all the foregoing problem or to achieve some of or all the foregoing effects. A technical feature which is not described as an essential feature in the present description may be appropriately deleted.

DESCRIPTION OF REFERENCE NUMERALS

10: gas sensor
100: sensor element
110: solid electrolyte body
112: bore
120: reference electrode
130: detection electrode
150: ceramic heater
151: heat generating portion
152: heater connection terminal
159, 160: packing
161: ceramic holder
162: sealing section
163: ceramic sleeve
164: metal ring
170: flange portion
180: protective layer
181: first catalyst layer
182: intermediate layer
183: second catalyst layer
184: outermost layer
200: metallic shell
210: threaded portion
220: flange portion
230: rear end portion
240: forward end portion
250: bore
252: crimp portion
260: step portion
300: protector
310: inner protector
311: gas introduction hole
313: gas discharge hole
320: outer protector
410: outer casing
411: forward end portion
412: rear end portion
510: connection terminal 520: inner connection terminal
530: outer connection terminal
570, 580: element lead wire
590: heater lead wire
600: separator
610: separator body
620: separator flange portion
630: lead wire insertion hole
640: holding hole
700: holding member
710: grommet
720: lead wire insertion hole
730: through hole
800: gas sensor
806: ceramic sleeve
807: sensor element
808: detection portion
810: metallic terminal member
821: first plate surface
823: second plate surface
830 to 834: electrode terminal
838: metallic shell
839: threaded portion
840: rear end portion
842: outer protector
843: inner protector
844: outer casing
846: lead wire
850: grommet
852: ledge
853: ceramic holder
854: through hole
856: talc ring
857: crimp packing
861: lead wire insertion hole
862: rear-end-side end face
865a: insertion portion
865b: groove
866: separator
867: flange portion
868: forward-end-side end face
869: holding member
871: insulating layer
872: surface protecting portion
872a: intermediate layer
872b: second catalyst layer
873: detection electrode
874: solid electrolyte body
875: reference electrode
876: insulating layer
877: heater
878: insulating layer
879: porous layer
900: filter unit
914, 916: through hole
932: detection lead portion
946: through hole
952: detection lead portion
972: heat generating portion
974: electrode terminal
984, 986: through hole
G: path of gas under measurement

The invention claimed is:

1. A gas sensor element used to detect a specific gas in a gas under measurement, the gas sensor element comprising:
a solid electrolyte body;
a first electrode disposed on a surface of the solid electrolyte body that is to be exposed to the gas under measurement;
a second electrode disposed on a surface of the solid electrolyte body; and
a protective layer containing a ceramic as a main component and disposed in a path through which the gas under measurement is supplied from the outside of the gas sensor element to the first electrode,
wherein the protective layer includes at least a first catalyst layer that supports a first catalyst metal other than a metal facilitating a reduction reaction of nitrogen oxide and a second catalyst layer that supports only a second catalyst metal facilitating the reduction reaction of the nitrogen oxide,
wherein the first catalyst layer and the second catalyst layer are arranged in the path in such a manner that the first catalyst layer and the second catalyst layer are not in direct contact with each other, and
wherein a space is provided between the first catalyst layer and the second catalyst layer.

2. The gas sensor element according to claim 1, wherein the protective layer further includes an intermediate layer composed only of a ceramic and disposed between the first catalyst layer and the second catalyst layer so as to be in contact with the first catalyst layer and the second catalyst layer.

3. The gas sensor element according to claim 2, wherein the intermediate layer has an average pore diameter larger than that of the outer one of the first catalyst layer and the second catalyst layer.

4. The gas sensor element according to claim 1, wherein each of the first catalyst layer and the second catalyst layer supports only one catalyst metal.

5. The gas sensor element according to claim 1, wherein the first electrode is a detection electrode, and
the second electrode is a reference electrode disposed on a surface of the solid electrolyte body that is to be exposed to a reference gas.

6. The gas sensor element according to claim 1, wherein one of the first catalyst layer and the second catalyst layer is formed so as to be adjacent to an outer surface of the first electrode, and
the first electrode contains a metal that is the same as the catalyst metal supported on the one of the first and second catalyst layers that is adjacent to the outer surface of the first electrode.

7. A gas sensor comprising the gas sensor element according to claim 1.

* * * * *